United States Patent [19]

Greco et al.

[11] Patent Number: 4,596,881
[45] Date of Patent: Jun. 24, 1986

[54] STABILIZED LIQUID ALUMINUM ALKOXIDES AND PROCESS

[75] Inventors: Carl C. Greco, Garnerville, N.Y.; Kelly B. Triplett, Stamford, Conn.

[73] Assignee: Stauffer Chemical Company, Westport, Conn.

[21] Appl. No.: 656,380

[22] Filed: Oct. 1, 1984

[51] Int. Cl.⁴ ............................................. C07F 5/06
[52] U.S. Cl. .................................................. 556/171
[58] Field of Search .................. 260/448 AD; 556/171

[56] References Cited

U.S. PATENT DOCUMENTS

| | | | |
|---|---|---|---|
| 2,687,423 | 8/1954 | Mesirow | 260/448 |
| 3,006,941 | 10/1961 | Mudrak et al. | 260/448 AD |
| 3,068,263 | 12/1962 | Smith | 260/448 AD |
| 3,405,154 | 10/1968 | Lundeen et al. | 260/448 AD |
| 3,450,735 | 6/1969 | Lundeen et al. | 260/448 AD |
| 3,538,168 | 11/1970 | Mitchell | 260/448 AD X |
| 3,655,423 | 4/1972 | Lin et al. | 117/47 |
| 3,761,500 | 9/1973 | Thomas | 260/448 AD |
| 3,904,550 | 9/1975 | Pine | 252/437 |
| 4,052,428 | 10/1977 | Lerner et al. | 260/448 AD |
| 4,287,131 | 9/1981 | Langer et al. | 260/448 R |

FOREIGN PATENT DOCUMENTS 7310958  4/1973  Japan .
7411759  3/1974  Japan .

OTHER PUBLICATIONS

"Alkoxides, Metal" by Britzinger and Josten, Kirk-Othmer's Encyclopedia of Chemical Technology, Third Edition, vol. 2, pp. 1–17, (1978).

Primary Examiner—Helen M. S. Sneed
Attorney, Agent, or Firm—Roger S. Benjamin

[57] ABSTRACT

A process is disclosed for reducing the solidification tendency of a normally solid lower aluminum alkoxide having 2 to 5 carbon atoms in the alkoxide radical. One embodiment comprises the steps of adding the aluminum alkoxide and a specific phosphorus compound to a common solvent, and forming a solution; and then extracting the common solvent to form a stabilized liquid. The phosphorus compound has an unblended structural formula

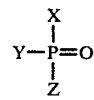

wherein X, Y and Z are selected from (a) alkoxy groups containing from one to 12 carbon atoms; (b) alkyl groups containing from one to 14 carbon atoms; (c) aryloxy groups containing from 6 to 12 carbon atoms; (d) alkyl-substituted aryloxy groups wherein an alkyl group containing from one to 14 carbon atoms is substituted for a hydrogen atom; (e) alkyl-substituted aryloxy groups containing from 7 to 26 carbon atoms; and (f) aryl-substituted alkyl groups containing from 7 to 26 carbon atoms. Preferred processing conditions and products thereby obtained are also disclosed.

21 Claims, No Drawings

STABILIZED LIQUID ALUMINUM ALKOXIDES AND PROCESS

BACKGROUND OF THE INVENTION (i) Field of the Invention

This invention relates generally to processes for stabilizing metal alkoxides to retain the same in fluid form during shipment and storage prior to use. It also relates generally to coating compositions comprising metal alkoxides and phosphorus-containing compounds as functional components. More particularly, it relates to aluminum alkoxides containing 2 to 5 carbon atoms per alkoxy radical which are stabilized against solidification/crystallization by the addition of minor amounts of specific organo phosphates. It also relates to the novel products thereby obtained.

(ii) Prior Art

Metal alkoxides are extremely old in the art. An excellent concise summary of their properties, end-uses, and methods of preparation is found in Kirk-Othmer's third Edition 1978, ISBN 0-471-02038-0, "Encyclopedia of Chemical Technology", Vol. 2, at pages 1–17 entitled "Alkoxides, Metal" by D. Bretzinger and W. Josten.

U.S. Pat. No. 2,687,423 (Mesirow) relates to stabilizing certain supercooled liquid lower alkyl aluminum alkoxides (having 2 to 4 carbon atoms in the alkoxide radical) against solidification, by the addition of critical amounts (5 to 40 wt. %) of aluminum trisecondary butoxide, $Al(OCHCH_3C_2H_5)_3$, itself an aluminum alkoxide. Mesirow theorizes that some interchange of alkoxide radicals may take place, particularly when the mixture is heated (see col. 3, lines 35 –60).

A computer search of Chemical Abstracts since 1967 for references relating to both metal alkoxides and phosphorus-containing compounds turned up only the five following references.

U.S. Pat. No. 4,287,131 (Langer et al.) discloses an invention wherein a metal alkoxide (particularly an aluminum alkoxide) "is contacted with phosphorus pentoxide in an inert liquid organic medium resulting in the production of an organo polyphosphate coordination complex with a metal compound. The resulting compounds have been found to be useful as polymer additives, corrosion inhibitors for functional fluids and as fire retardants for cellulosic materials." However, Langer does not relate to the use of an organic phosphorus compound as raw material. Nor does Langer relate to a product that is a liquid (but rather a gel).

U.S. Pat. No. 3,655,423 (Lin et al.) particularly "relates to a process for applying organic coating compositions or organic films such as siccative coatings, dyes, adhesives and the like to substrates which have been subjected to a low oxidation state phosphorus compound which can be prepared by reacting elemental phosphorus with a nucleophilic reagent or organometallic compound." Lin does not relate to the use of a phosphorus compound having an oxidation state of 5.

Japanese Pat. No. 7411759 (Oda et al.) relates to the catalytic polymerization of alkylene oxide. According to the CA Abstract, the catalyst may be alkoxides-phosphorus halides; . . . phosphorus halide; . . . aluminum isopropoxide." It appears to be less relevant than the aforementioned art.

Japanese Pat. No. 7310958 relates to the catalytic polymerization of epoxides. According to the CA Abstract, the catalyst may be metal alkoxides or alkoxide halides containing phosphorus esters. The only metals listed in the abstract are titanium, zirconium and hafnium. Aluminum is not listed therein. Accordingly, it also appears to be less relevant than the aforementioned prior art.

In addition, U.S. Pat. No. 3,904,550 (Pine) is of interest in that it relates to:

"the reaction in aqueous medium of aluminum alkoxide with a phosphorus-containing acid or soluble salt thereof at an aluminum alkoxide/phosphate ion molar ratio in the range of 26:1 to 1.2:1, said phosphorus-containing acid having the formula:

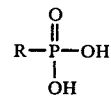

wherein R respresents a hydroxyl group, hydrogen or a hydrocarbon radical containing from 1 to 12 carbon atoms" (see Pine, claim 1).

SUMMARY OF THE INVENTION

In contrast to the aforementioned prior art, it has been found that if an aluminum alkoxide or mixtures of aluminum alkoxides which normally solidify to the hard crystalline state has intimately blended with it a critical amount of an organo phosphate such as tributyl phosphate, the mixed product will have enhanced stability as a liquid. The time during which the mixture remains a liquid is extended for a considerable or indefinite time. The products are useful as coating compositions and in preparing aluminum aircraft components and graphite fiber/resin composites. In its broadest aspect, the product of the invention is as follows:

A stabilized liquid blend of a normally solid lower aluminum trialkoxide having 2 to 5 carbon atoms in each alkoxide group which comprises a phosphorus compound being present in an amount of from 5 weight percent to 40 weight percent based on the weight of the mixture, wherein the phosphorus compound has an oxidation state of 5, and an unblended structural formula

wherein X, Y and Z are defined in the following manner: X, Y and Z are selected from (a) alkoxy groups containing from one to 12 carbon atoms; (b) alkyl groups containing from one to 14 carbon atoms; (c) aryloxy groups containing from 6 to 12 carbon atoms: (d) alkyl-substituted aryloxy groups wherein an alkyl group containing from one to 14 carbon atoms is substituted for a hydrogen atom: (e) alkyl-substituted aryloxy groups containing from 7 to 26 carbon atoms; and (f) aryl-substituted alkyl groups containing from 7 to 26 carbon atoms.

DESCRIPTION OF THE PREFERRED EMBODIMENTS

The preferred embodiments of the invention are described below and in the claims hereinafter.

At the outset, it should be noted that the mechanism by which stabilization occurs is not fully understood, even with the benefit of hindsight; but it is believed to be both physical and chemical in nature. Accordingly, all of the terms used herein to characterize the products formed by blending should be broadly construed so as not to exclude the possibility of chemical reaction(s) being present. Such terms include "stabilized liquid blend"; "mixed product"; "mixture"; "blended products"; "melt blend"; and "blend".

Essentially, the Examples and the Comparative Examples below show the following. Aluminum alkoxides containing 2-5 carbon atoms per alkoxy radical can be stabilized in the liquid state by the intimate addition of a minor amount of tributyl phosphate; dimethyl methylphosphonate; butylated triphenyl phosphate; and iso-decyl diphenyl phosphate. Interestingly, tris-chloro isopropyl phosphate is ineffective. Of course, the invention is not limited to the specific working Examples shown herein.

The phosphorus compounds used in the invention are preferably those wherein at least two of X, Y and Z are identical groups; and most preferably alkoxy or phenoxy groups. It is more preferred that X, Y and Z all be identical alkoxy groups. Tributyl phosphate is particularly preferred. It is also preferred that the phosphorus compound be a liquid at room temperature, and that it contain from 4 to 30 carbon atoms.

Examples of aluminum alkoxide that may be stabilized by use of the invention include the following and mixtures thereof: aluminum triisopropoxide, aluminum triethoxide, aluminum tri-n-butoxide, aluminum tri-n-pentoxide and diisobutyl, n-butyl aluminum alkoxide.

It is preferred that the blend comprise from about 10 to about 30 weight percent of the phosphorus compound, based on the weight of the final stabilized blend.

A first preferred process of the invention (as shown in Examples 1 and 2) comprises the steps of: [1] adding together the aluminum alkoxide, the phosphorus compound, and a solvent, S, wherein S is a common solvent for the aluminum alkoxide and the phosphorus compound, thereby forming a mixture M1: [2] intimately mixing M1 to form a solution, M2; and [3] extracting S from M2 to form a stabilized liquid, M3. In such a process it is preferred that M1 be heated to a temperature of up to 100° C. in step [1] and that vacuum be employed to remove the common solvent in step [2]. Many well known solvents may be used. Those having boiling points over 100° C. are preferred. Toluene is a particularly convenient solvent to use in many cases.

A second preferred process of the invention (as shown in Examples 3 and 4) involves melt blending of the liquid aluminum alkoxide with liquid organo phosphate, without use of a solvent.

Examples of the invention and some Comparative Examples now follow. The invention, of course, is not limited to the Examples shown herein.

COMPARATIVE EXAMPLE C-1

A sample of di-isobutyl, n-butyl aluminum alkoxide was conventionally prepared in the following manner. 27.0 grams of aluminum powder, 171 grams of isobutyl alcohol and 73.4 grams of n-butyl alcohol were mixed together with 0.2 grams of $HgCl_2$ and allowed to reflux for 24 hours. The mixture was filtered to remove unreacted aluminum metal, and the filtrate distilled to constant weight. The remaining material was a sample of di-isobutyl, n-butyl aluminum alkoxide.

A portion of the freshly prepared sample was found to set to a solid crystalline mass by standing only a few minutes at room temperature.

EXAMPLE 1

Di-isobutyl, n-butyl aluminum alkoxide was prepared exactly as in Comparative Example C-1. A portion of the freshly prepared material (60.8 grams) was immediately mixed with 12.7 grams of tributyl phosphate and 67 grams of toluene. The mixture was heated to 65° C. under vacuum to remove the toluene and also to mix the tributyl phosphate and aluminum alkoxide composition. A blend was obtained which was permanently stable, as indicated by no signs of crystallization after several weeks at room temperature.

EXAMPLE 2

Freshly prepared di-isobutyl, n-butyl aluminum alkoxide was heated with dimethyl methylphosphonate at 60°-70° C. at the 15 weight percent level. This blend remained stable and did not solidify for over one week.

EXAMPLE 3

Di-isobutyl, n-butyl aluminum alkoxide was prepared exactly as in Comparative Example C-1. A portion of the freshly prepared material (50.0 grams) was immediately mixed with 21.4 grams of butylated triphenyl phosphate (Stauffer Chemical Company's PHOSFLEX TM 71B, which is monobutylated on the average). The liquid mixture was heated in an oil bath to a temperature of about 65°-100° C., with stirring by intermittent handshaking, for about 30 minutes; and then allowed to cool to room temperature. The blend was still a viscous liquid after 14 days.

EXAMPLE 4

Di-isobutyl, n-butyl aluminum alkoxide was prepared exactly as in Comparative Example C-1. A portion of the freshly prepared material (58.0 grams) was immediately mixed with 21.4 grams of iso-decyl diphenyl phosphate (Stauffer Chemical Company's PHOSFLEX TM 390). The liquid mixture was heated in an oil bath to a temperature of about 65°-100° C., with stirring by intermittent hand shaking, for 30 minutes; and then allowed to cool to room temperature. The blend was still a viscous liquid after 14 days.

COMPARATIVE EXAMPLE C-2

The procedures of Examples 3 and 4 were essentially repeated except that 11.85 grams of tris-chloro ispropyl phosphate (Stauffer Chemical Company's PCF) was blended with 27.65 grams of the freshly prepared aluminum alkoxide. However, within a few minutes of the heated blend being cooled to room temperature, it solidified.

What we claim is:

1. A stabilized liquid blend composition of a normally solid lower aluminum trialkoxide having 2 to 5 carbon atoms in each alkoxide group which comprises a phosphorus compound being present in an amount of from 5 weight percent to 40 weight percent based on the weight of the mixture, wherein the phosphorus compound has an oxidation state of 5, and an unblended structural formula

wherein X, Y and Z are defined in the following manner: X, Y and Z are selected from (a) alkoxy groups containing from one to 12 carbon atoms: (b) alkyl groups containing from one to 14 carbon atoms; (c) aryloxy groups containing from 6 to 12 carbons atoms; (d) alkyl-substituted aryloxy groups wherein an alkyl group containing from one to 26 carbon atoms is substituted for a hydrogen atom; and (e) aryl-substituted alkyl groups containing from 7 to 26 carbon atoms.

2. The blend of claim 1, wherein the phosphorus compound is essentially halogen-free.

3. The blend of claim 1, wherein at least two of X, Y, and Z are identical.

4. The blend of claim 1 wherein X, Y and Z are identical.

5. The blend of claim 1 wherein the phosphorus compound is tributyl phosphate or dimethyl methylphosphonate or butylated triphenyl phosphate or iso-decyl dipheny phosphate or mixtures thereof.

6. The blend of claim 1 wherein the aluminum trialkoxide is selected from the group consisting of aluminum triisopropoxide, aluminum tripropoxide, aluminum triethoxide, aluminum tri-n-butoxide, aluminum tri-n-pentoxide, and di-isobutyl, n-butyl aluminum alkoxide or mixtures thereof.

7. The blend of claim 1 which comprises a phosphorus compound that is a liquid at 20° C.

8. The blend of claim 1, wherein the phosphorus compound contains at least 4 carbon atoms.

9. The blend of claim 1, wherein the phosphorus compound contains up to 30 carbon atoms.

10. The blend of claim 1 which comprises from 10 weight percent to 30 weight percent of the phosphorus compound.

11. A process of reducing the solidification tendency of a normally solid lower aluminum alkoxide having 2 to 5 carbon atoms in the alkoxide radical, comprising blending an aluminum alkoxide with at least 5 weight percent of a phosphorus compound based on the weight of the mixture, wherein the phosphorus compound has an oxidation state of 5 and the structural formula:

wherein X, Y, and Z are defined in the following manner: X, Y and Z are selected from (a) alkoxy groups containing from one to 12 carbon atoms; (b) alkyl groups containing from one to 14 carbon atoms; (c) aryloxy groups containing from 6 to 12 carbon atoms; (d) alkyl-substituted aryloxy groups wherein an alkyl group containing from one to 26 carbon atoms is substituted for a hydrogen atom; and (e) aryl-substituted alkyl groups containing from 7 to 26 carbon atoms.

12. The process of claim 11 which comprises blending freshly prepared liquid aluminum alkoxide.

13. The process of claim 11 which comprises blending up to 40 weight percent of the phosphorus compound.

14. The process of claim 11 which comprises the steps of:
(1) adding together the aluminum alkoxide, the phosphorus compound and a solvent, S, wheren S is a common solvent for the aluminum alkoxide and phosphorus compound, thereby forming a mixture M1;
(2) intimately mixing M1 to form a solution, M2; and
(3) extracting S from M2 to form a stabilized liquid, M3.

15. The process of claim 14 which comprises heating M1 to a temperature up to 100° C.

16. The process of claim 15 which comrises applying a vacuum to M2 to remove the solvent, S.

17. The process of claim 14 wherein step (1) comprises using toluene as the solvent S.

18. The process of claim 14 wherein step (1) comprises adding together di-isobutyl, n-butyl aluminum alkoxide and tributyl phosphate or dimethyl methylphosphonate and the common solvent.

19. The process of claim 11 which comprises melt blending a liquid aluminum alkoxide and a liquid organo phosphate in the absence of a solvent.

20. A process of reducing the solidification tendency of a normally solid lower aluminum alkoxide having 2 to 5 carbon atoms in the alkoxide radical, comprising melt blending in the absence of a solvent a liquid aluminum alkoxide with at least 5 wt. % of monobutylated triphenyl phosphate or iso-decyl diphenyl phosphate.

21. The process of claim 19 which comprises melt blending a liquid aluminum alkoxide and a liquid organo phosphate wherein at least 2 of the X, Y and Z groups in the structural formula of the phosphorus compound are identical groups selected from the group consisting of alkoxy or phenoxy groups.

* * * * *